(12) United States Patent
Nakatani et al.

(10) Patent No.: US 7,736,477 B2
(45) Date of Patent: Jun. 15, 2010

(54) PROBE FOR MEASURING ELECTRIC POTENTIAL OF CELL

(75) Inventors: Masaya Nakatani, Hyogo (JP); Nobuhiko Ozaki, Nara (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 770 days.

(21) Appl. No.: 10/595,275

(22) PCT Filed: Jul. 14, 2005

(86) PCT No.: PCT/JP2005/013029

§ 371 (c)(1),
(2), (4) Date: Apr. 4, 2006

(87) PCT Pub. No.: WO2006/022092

PCT Pub. Date: Mar. 2, 2006

(65) Prior Publication Data

US 2007/0105183 A1    May 10, 2007

(30) Foreign Application Priority Data

Aug. 25, 2004  (JP) .............................. 2004-245574
Nov. 8, 2004   (JP) .............................. 2004-323358

(51) Int. Cl.
*G01N 33/487* (2006.01)
(52) U.S. Cl. .............................. 204/403.01; 435/287.3; 205/777.5
(58) Field of Classification Search ................. 204/400, 204/403.01, 601; 422/50; 73/864; 436/63; 604/900, 902; 435/29, 287.3; 250/306–307; 205/777.5, 775
See application file for complete search history.

(56) References Cited

U.S. PATENT DOCUMENTS 2,366,654 A * 1/1945 Rotter et al. ................. 417/295

(Continued)

FOREIGN PATENT DOCUMENTS

JP    2-131569    5/1990

(Continued)

OTHER PUBLICATIONS

Taylor, G.I. "The Criterion for Turbulence in Curved Pipes." Proceedings of the Royal Society of London. Series A, Containing Papers of a Mathematical and Physical Character (1905-1934), vol. 124, #794, pp. 243-249. Royal Society Publishing, Jun. 4, 1929.*

(Continued)

*Primary Examiner*—Kaj K Olsen
(74) *Attorney, Agent, or Firm*—Wenderoth, Lind & Ponack, L.L.P.

(57) ABSTRACT

A probe for measuring an electric potential of a cell includes a plate having a surface having a first cavity provided therein, and a sensor element provided in the first cavity. A second cavity is provided in the bottomsurface of the first cavity. The first flow passage having first and second openings is provided in the plate. The first and second openings of the first flow passage open to the second cavity and outside the plate, respectively. The sensor element includes a thin plate, and a supporting substrate provided around the thin plate and in the first cavity of the plate. The thin plate has a through-hole therein having a first opening and a second opening communicating with the second cavity of the plate. The first flow passage allows fluid to flow therein. A sucking device is coupled with the second opening of the first flow passage as to suck the fluid flowing in the first flow passage. This probe can measure an electric potential of a cell floating in solution as it is in this environment.

31 Claims, 16 Drawing Sheets

U.S. PATENT DOCUMENTS

| | | | |
|---|---|---|---|
| 4,704,255 A * | 11/1987 | Jolley | 422/101 |
| 5,183,744 A | 2/1993 | Kawamura et al. | |
| 6,682,649 B1 | 1/2004 | Petersen et al. | |
| 6,984,297 B2 | 1/2006 | Nisch et al. | |
| 7,006,929 B2 | 2/2006 | Oka et al. | |
| 7,501,278 B2 | 3/2009 | Nakatani et al. | |
| 2002/0063067 A1 * | 5/2002 | Bech et al. | 205/775 |
| 2002/0074227 A1 | 6/2002 | Nisch et al. | |
| 2003/0032946 A1 * | 2/2003 | Fishman et al. | 604/890.1 |
| 2003/0113833 A1 | 6/2003 | Oka et al. | |
| 2003/0132109 A1 * | 7/2003 | Bullen et al. | 204/403.01 |
| 2004/0033483 A1 | 2/2004 | Oka et al. | |
| 2005/0221469 A1 | 10/2005 | Nakatani et al. | |

FOREIGN PATENT DOCUMENTS

| | | |
|---|---|---|
| JP | 2003-511668 | 3/2003 |
| JP | 2003-511699 | 3/2003 |
| JP | 2004-163 | 1/2004 |
| JP | 2004-12215 | 1/2004 |
| JP | 2004-69309 | 3/2004 |
| JP | 2004-271330 | 9/2004 |
| JP | 2004-271331 | 9/2004 |
| WO | 02/055653 | 7/2002 |
| WO | 02/99408 | 12/2002 |
| WO | 03/16555 | 2/2003 |

OTHER PUBLICATIONS

Wolf, Julie B. "Transformation of *E. coli* by Electroporation." Jan. 17, 2006. <http://userpages.umbc.edu/~jwolf/m7.htm>.*

* cited by examiner

PROBE FOR MEASURING ELECTRIC POTENTIAL OF CELL

TECHNICAL FIELD

The present invention relates to a probe for measuring an electric potential of a cell, such as an intracellular potential or an extracellular potential, used for measuring physicochemical change produced by activity of the cell.

BACKGROUND OF THE INVENTION

A patch clamping method is known as a conventional method of screening candidate pharmaceuticals by monitoring electrical activity of a cell in order to select effective pharmaceutical. In the patch clamping method, a hollow glass tube having a microscopic tip is inserted directly into a cell, thereby measuring a difference between an inside and outside of the cell. (For instance, "Single Channel Currents Recorded From Membrane of Enervated Frog Muscle Fibers", Nature 260: 799-802, Neher E & Sakmann B, 1976) This method provides accurate measurement of the status of activities of an ion channel existing in a cell membrane.

International Publication No. WO02/055653 discloses a device and a method for measuring an extracellular electric potential. This device includes a substrate having a holding section and electrodes to measure an extracellular electric potential. This device provides data as accurate as data provided by the patch clamping method, and measures a large amount of samples easily and quickly.

FIG. 24 is a sectional view of the above-mentioned device for measuring an extracellular electric potential. Culture solution 51 is put in container 50. Target cell 52 is caught and held with the holding section provided at substrate 53. This holding section is formed with cavity 54, opening 55, and through-hole 56 which are all formed in substrate 53, and hole 56 communicating with cavity 54. Reference electrode 58 is provided in container 50. Measuring electrode 57 is provided near through-hole 56. Electrode 57, a sensing section, is coupled to an external signal detector via wiring.

Target cell 52 is sucked via through-hole 56 by a suction pump from the outside, contacts cavity 54, thus being held at cavity 54. Electrical signals produced by activity of target cell 52 is detected as an electric potential difference between measuring electrode 57 disposed near through-hole 56 and reference electrode 58 without leakage into culture solution 51.

This conventional device includes substrate 53 having cavity 54 and through-hole 56 formed therein and container 50 provided on substrate 53. Container 50 is used for receiving and storing culture solution and chemicals. This structure, therefore, cannot measure electric potentials of cells floating in the solution in a large space as it is in this environmental condition.

The conventional device has two areas partitioned with substrate 53, namely, one area having target cell 52 therein and the other area having measuring electrode 57, and cannot introduce respective culture solutions or chemicals different from each other into the areas.

SUMMARY OF THE INVENTION

A probe for measuring an electric potential of a cell includes a plate having a surface having a first cavity provided therein, and a sensor element provided in the first cavity. A second cavity is provided in the bottom surface of the first cavity. The first flow passage having first and second openings is provided in the plate. The first and second openings of the first flow passage open to the second cavity and outside the plate, respectively. The sensor element includes a thin plate, and a supporting substrate provided around the thin plate and in the first cavity of the plate. The thin plate has a through-hole therein having a first opening and a second opening communicating with the second cavity of the plate. The first flow passage allows fluid to flow therein. A sucking device is coupled with the second opening of the first flow passage as to suck the fluid flowing in the first flow passage.

This probe can measure an electric potential of a cell floating in solution as it is in a current environment.

REFERENCE NUMERALS

1 Probe for Measuring Electric Potential of Cell
2 Plate
2A Molded Plate
2B Molded Plate
3 Cavity (First Cavity)
4 Sensor Element
5 Cavity (Third Cavity)
6 Cavity (Second Cavity)
7 Supporting Substrate
8 Thin Plate
9 Through-Hole
10 Flow Passage (Second Flow Passage)
10A Opening (First Opening)
11 Flow Passage (First Flow Passage)
11A Opening (First Opening)
12 Opening (Second Opening)
13 Sucking Device
15 Container (Pouring Device)
16 Measurement Solution
17 Bump
18 Reference Electrode (First Electrode)
19 Measuring Electrode (Second Electrode)
20 Target Cell
21 Culture Solution
22 Opening (Second Opening)
23 Valve
26 Supporting Substrate
27 Probe for Measuring Electric Potential of Cell
28 Plate
29 Sensor Element
30 Thin Plate
31 Through-Hole
32 Cavity
33 Microscope
34 Patch Probe
35 Target Cell
36 Culture Solution
37A, 37B Recess
117 Bump
501 Probe for Measuring Electric Potential of Cell
502 Plate
503 Cavity (First Cavity)
504 Sensor Element
505 Cavity (Third Cavity)
506 Cavity (Second Cavity)
507 Thin Plate
508 Through-Hole
509 Flow Passage (Second Flow Passage)
510 Flow Passage (First Flow Passage)
511 Opening (Second Opening)
512 Supporting Substrate
514 Reference Electrode (First Electrode)
515 Measuring Electrode (Second Electrode)
518 Opening (Second Opening)
519 Probe Array for Measuring Electric Potential of Cell
520 Well Array
521A Through-Hole
521B Through-Hole
521C Through-Hole
522 Well
523 Well
524 Well

DETAIL DESCRIPTION OF THE PREFERRED EMBODIMENTS

Exemplary Embodiment 1

Figure 1:
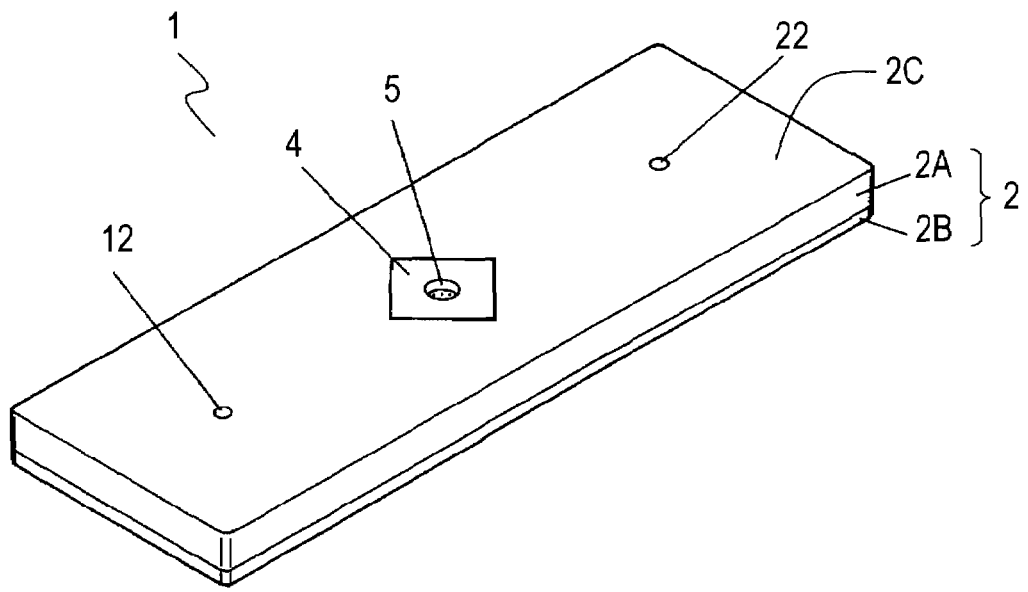
FIG. 1 is a perspective view of a probe for measuring an electric potential of a cell in accordance with Exemplary Embodiment 1 of the present invention.
Figure 2:
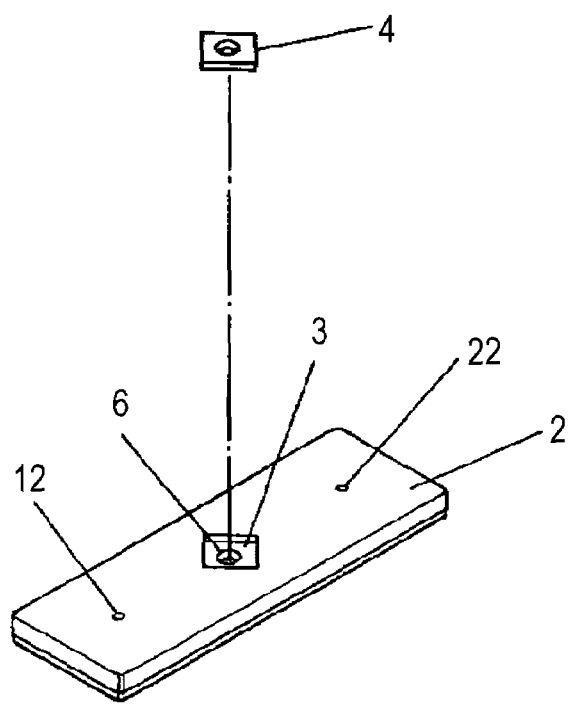
FIG. 2 is an exploded perspective view of the probe in accordance with Embodiment 1.
Figure 3:
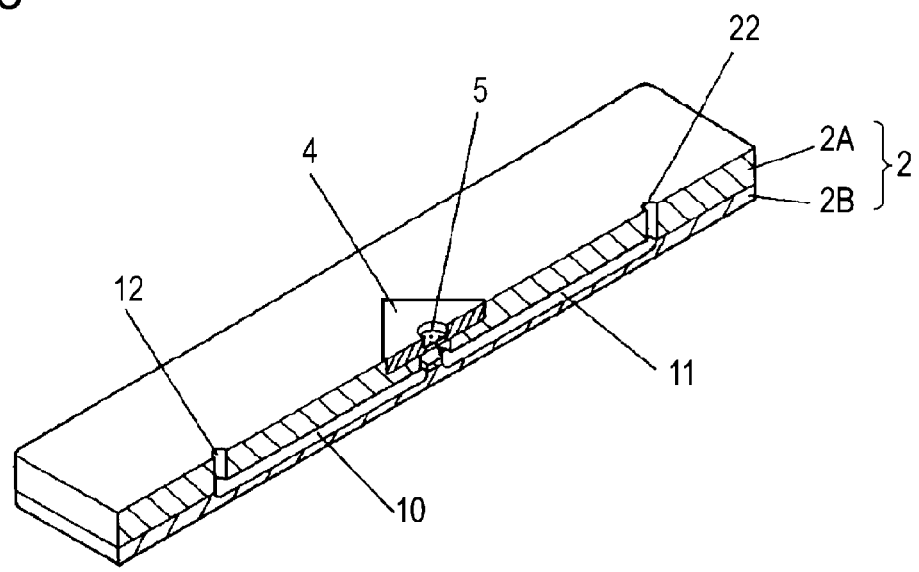
FIG. 3 is a sectional perspective view of the probe in accordance with Embodiment 1.
Figure 4:
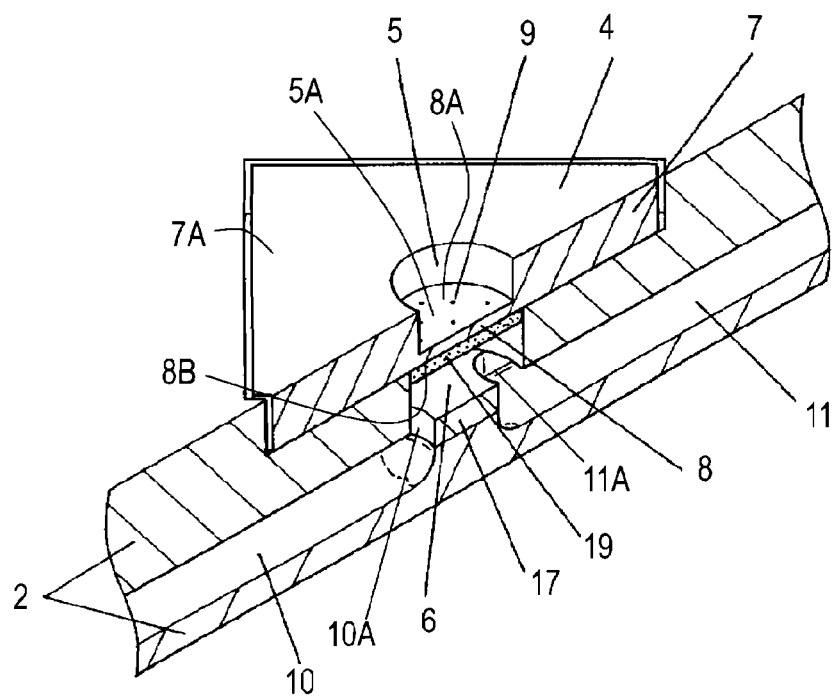
FIG. 4 is an enlarged sectional perspective view of the probe in accordance with Embodiment 1.
Figure 5:
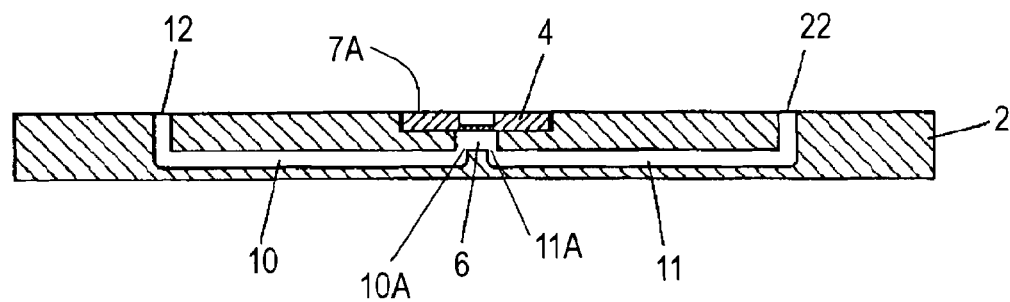
FIG. 5 is a sectional view of the probe in accordance with Embodiment 1.
Figure 6:
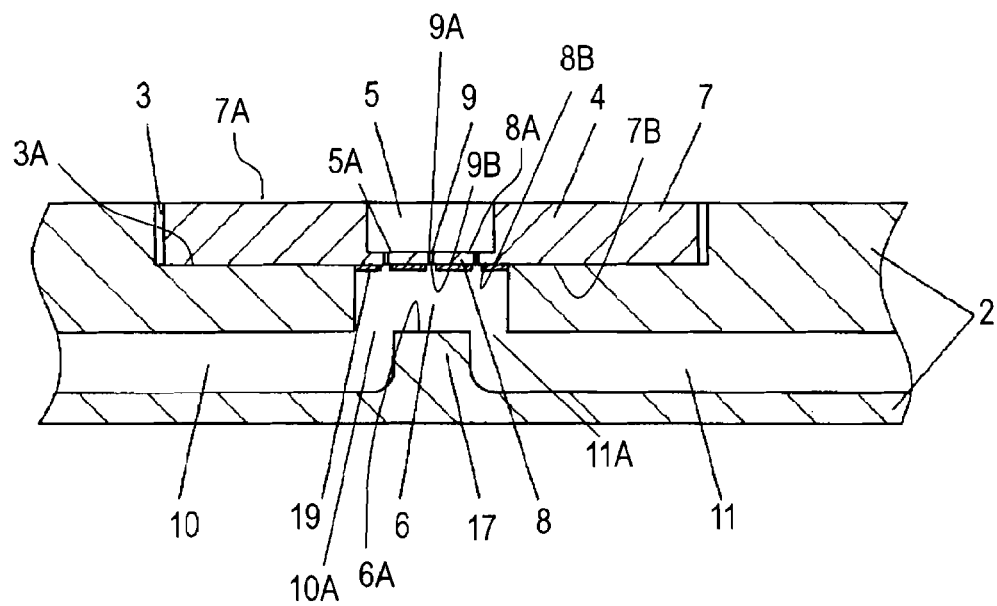
FIG. 6 is an enlarged sectional view of the probe in accordance with Embodiment 1.

FIG. 1 is a perspective view of probe 1 for measuring an electric potential of a cell in accordance with Exemplary Embodiment 1 of the present invention. FIG. 2 is an exploded perspective view of probe 1. FIG. 3 is a sectional perspective view of probe 1. FIG. 4 is an enlarged sectional perspective view of probe 1. FIG. 5 is a sectional view of probe 1. FIG. 6 is an enlarged sectional view of an essential part of probe 1. Probe 1 includes sensor element 4 and plate 2 made of insulating material, such as resin or glass. Plate 2 has cavity 3 provided in upper surface 2C thereof. Sensor element 4 is fit into cavity 3. Cavity 6 is provided under bottom surface 3A of cavity 3. Cavity 6 is positioned under sensor element 4.

Plate 2 includes molded plate 2A and molded plate 2B attached onto plate 2A, and can be shaped in a complicated shape easily. Plate 2B has flow passages 10 and 11 having groove shapes. Plate 2A has openings 12 and 22 shaped like through-holes. Cavity 3 shaped like a through-hole and cavity 6 communicate with each other.

Cavity 6 communicates with openings 10A and 11A of flow passages 10 and 11 communicating with the outside of plate 2, respectively. Other openings 12 and 22 of flow passages 10 and 11 open to upper surface 2C of plate 2, respectively. The sectional area of each of flow passages 10 and 11 is not smaller than 0.01 mm$^2$ to so as preventing flow passages 10 and 11 from being clogged and so as to enable the passages to be cleaned easily.

Lower surface 6A of cavity 6 has bump 17 thereon projecting toward sensor element 4, i.e. projecting upward towards cavity 6. This structure enables the adjusting of the sectional areas of flow passages 10 and 11 and the sectional areas of the vicinity of openings 10A and 11A at cavity 6, so that solution to be used for measuring can move smoothly through flow passage 10, cavity 6, and flow passage 11.

Sensor element 4 includes supporting substrate 7 made of a silicon substrate or a laminated body including a silicon substrate and a silicon-dioxide film on the silicon substrate. Upper surface 7A of supporting substrate 7 faces towards a direction identical to a direction towards which upper surface 2C of plate 2 faces, and has cavity 5 provided therein. Thin plate 8 provides bottom surface 5A of cavity 5. Thin plate 8 has through-holes 9 having small diameters allowing upper surface 8A (bottom surface 5A of cavity 5) to communicate with lower surface 8B of thin plate 8. One opening 9A of each of through-holes 9 opens to cavity 5, and another opening 9B of each of through-holes 9 communicates with cavity 6 provided in plate 2.

Measuring electrode 19 made of platinum, gold, silver, or silver chloride is provided on lower surface 8B of thin plate 8, i.e., on lower surface 7B of supporting substrate 7 of sensor element 4. Measuring electrode 19 is connected with a lead electrode made of a wire or a thin-film electrode for which connecting the measuring electrode with a measuring instrument outside probe 1 for detecting a signal.

Sensor element 4 is bonded so securely into cavity 3 with an adhesive so that the solution (measurement solution) to be used for measurement filling passages 10 and 11 and cavity 6 can be prevented completely from leakage. Sensor element 4 may be bonded into cavity 3 by fusion bonding or ultrasonic bonding.

Figure 7:
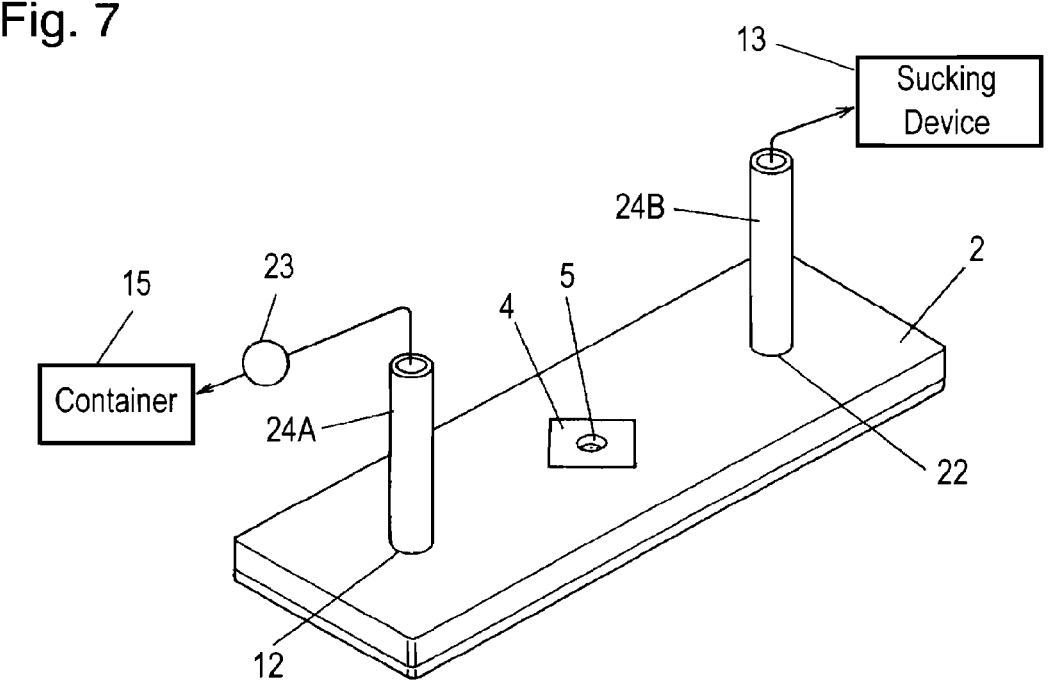
FIG. 7 is a perspective view of the probe in accordance with Embodiment 1.

FIG. 7 is a perspective view of probe 1 for measuring an electric potential of a cell. Tube 24A is connected with opening 12 of flow passage 10. Tube 24B is connected with flow passage 11. Tube 24B is connected with sucking device 13, and tube 24A is connected with container 15. Valve 23 is provided between container 15 and opening 12 to stop the flow of fluid, such as the measurement solution, upon necessary. Sucking device 13 provides cavity 6 with decompressed atmosphere therein having a pressure lower than that in cavity 5. Sucking device 13 may be an ordinary pump, such as a diaphragm pump, a syringe pump, or sucking with a human mouth, and is not limited to these.

A method of measuring an electric potential of a cell with probe 1 will be described below.

Figure 8:
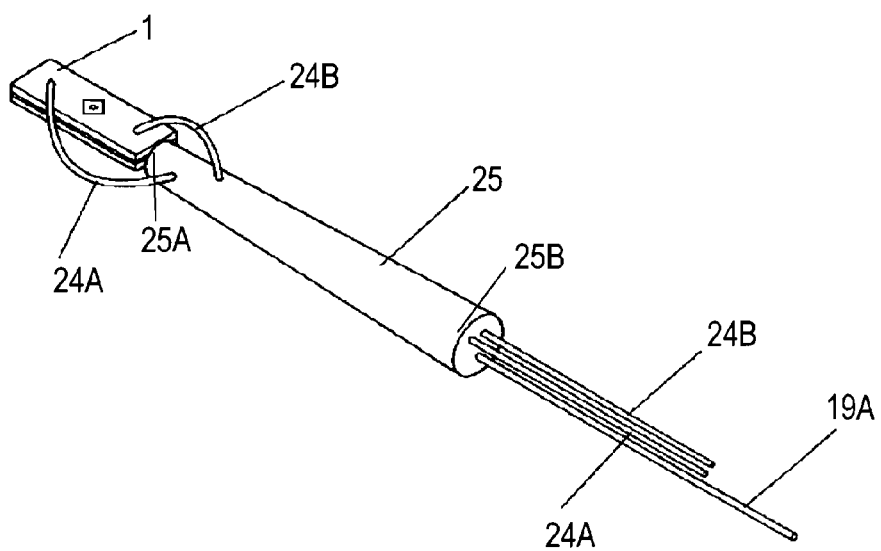
FIG. 8 is a perspective view of the probe for illustrating its usage in accordance with Embodiment 1.

FIG. 8 is a perspective view of probe 1 for illustrating its usage. Probe 1 is mounted to measuring stick 25. Probe 1 is fixed to end 25A of measuring stick 25. Tube 24A coupled with flow passage 10, tube 24B coupled with flow passage 11, and electrode wire 19A electrically coupled with measuring electrode 19 are arranged inside stick 25, and are drawn out from another end 25B of stick 25. Electrode wire 19A is connected with an external measuring instrument for supplying measured signals to the instrument.

Figure 9:
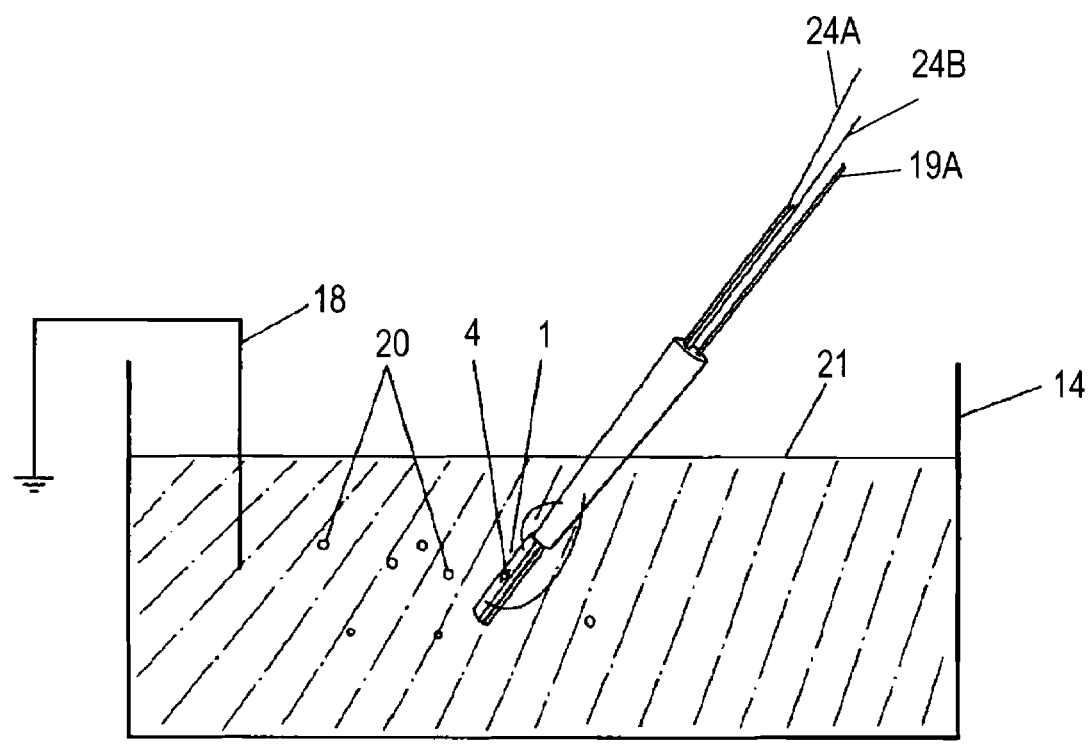
FIG. 9 is a schematic diagram of the probe in accordance with Embodiment 1.

FIG. 9 is a schematic diagram of probe 1 which being used. Measuring stick 25 having probe 1 mounted thereto is dipped into culture solution 21 stored in container 14. Target cells 20 float in solution 21. Reference electrode 18 contacts solution 21 in container 14, thus sensing an electric potential of solution 21 in container 14. Probe 1 is positioned so that sensor element 4 can be dipped in solution 21.

FIGS. 10 to 14 are sectional views of probe 1 for illustrating a method for measuring an electric potential of a cell with the probe.

Figure 10:
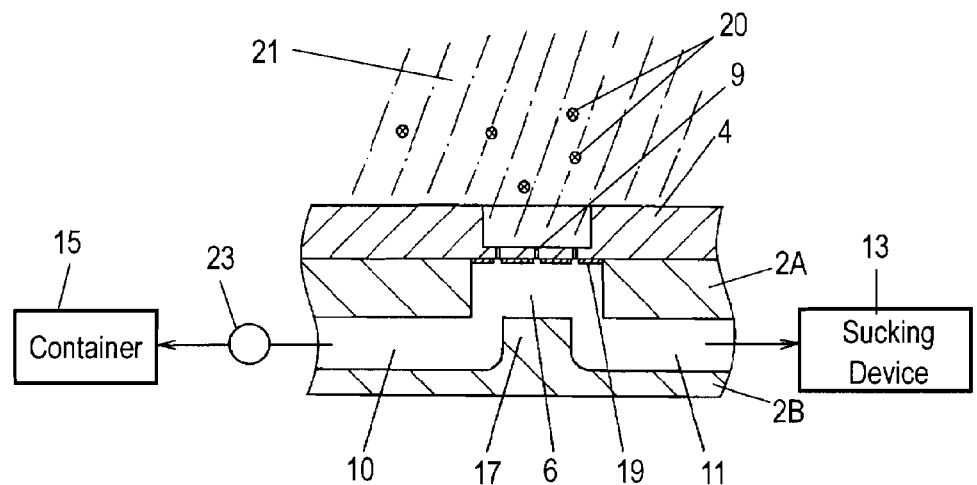
FIG. 10 is a sectional view of the probe in accordance with Embodiment 1.

As shown in FIG. 10, target cells 20 float above sensor element 4 in solution 21.

Figure 11:
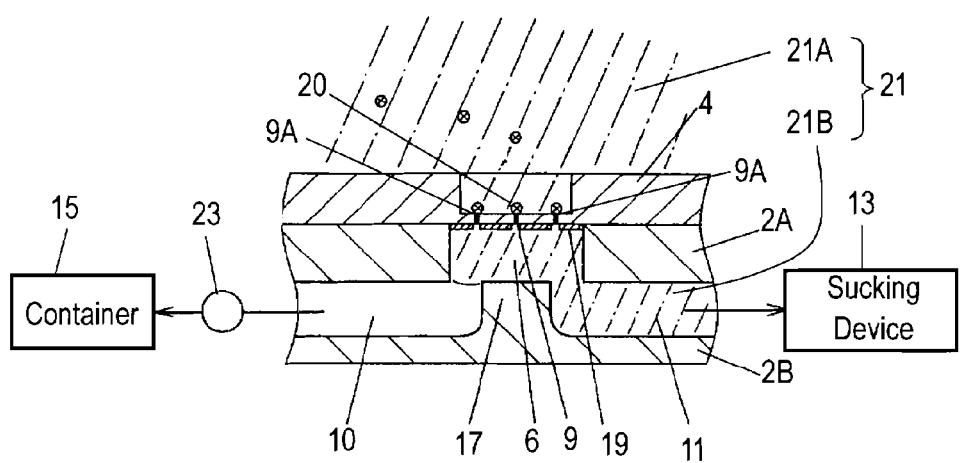
FIG. 11 is a sectional view of the probe in accordance with Embodiment 1.

Next, as shown in FIG. 11, valve 23 is closed so that flow passages 10 and 11 and cavity 6 are shut off from container 15. Then, cavity 6 is decompressed by sucking device 13 to have a pressure therein lower than that in cavity 5. This operation causes solution 21 and cells 20 filling cavity 5 to be sucked towards through-holes 9, and then, causes solution 21 to flow into cavity 6. Each of cells 20 has a size larger than the sectional area of through-hole 9, and hence, does not pass through through-holes 9, thus being held at openings 9A of holes 9. Solution 21 flowing into cavity 6 contacts measuring electrode 19, thereby allowing an electric potential in cavity 6 to be detected. In this situation, a difference between respective electric potential of reference electrode 18 and measuring electrode 19, an electrical resistance between the electrodes, and a capacitance between the electrodes can be measured.

When target cells 20 are held at openings 9A of through-holes 9, sensor element 4 separates culture solution 21 into portion 21A in cavity 5 and portion 21B in cavity 6, thereby increases the resistance between reference electrode 18 and measuring electrode 19.

Figure 12:
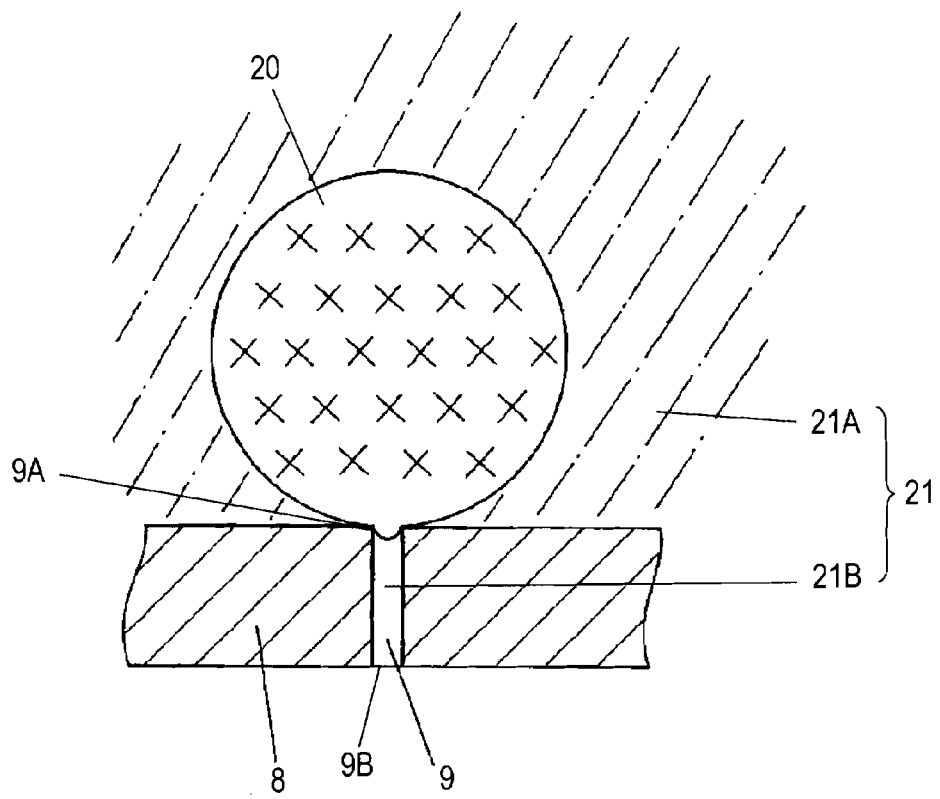
FIG. 12 is a sectional view of the probe in accordance with Embodiment 1.

Then, cavity 6 is further decompressed by sucking device 13, and accordingly, as shown in FIG. 12, the surface of target cell 20 is urged more strongly onto opening 9A of hole 9, accordingly providing the resistance between electrodes 18 and 19 larger than that of the case that cell 20 is merely held at opening 9A. At this moment, the resistance exceeds 100 M$\Omega$ and may exceed 1 G$\Omega$, which is called "Giga-Seal". In the Giga-Seal, an ion-channel activity of cells 20 causes ion exchange between culture solution 21 and cells 20, thereby changing an inner electric potential of each of cells 20. This change can be detected as the difference between respective electric potentials of reference electrode 18 and measuring electrode 19.

The ion channel activity changes according to pharmaceutical contained in culture solution 21, and is detected as the difference of respective electrical potentials of electrodes 18 and 19 so as to detect an influence to target cells 20, thus allowing a pharmaceutical chemically effect to cells 20 to be determined.

Reference electrode 18 and measuring electrode 19 are arranged near openings 9A and 9B of through-holes 9, respectively, to measure the electric potential difference around cell 20 accurately. Probe 1 can catch cells 20 floating in solution 21 easily to provide the Giga-Seal.

Figure 13:
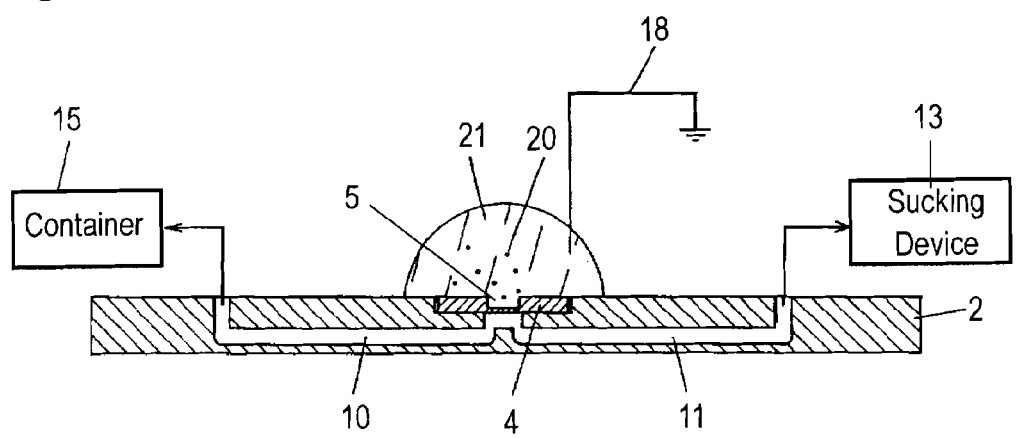
FIG. 13 is a sectional view of the probe in accordance with Embodiment 1.

Upper surface 2A of plate 2 is flush with upper surface 7A of supporting substrate 7, and hence, solution 21 including cells 20 can be directly supplied onto upper surface 7A of supporting substrate 7 or into cavity 5 with a plate pipette, as shown in FIG. 13. This arrangement allows cells 20 to be observed easily with a microscope from above upper surface 2C of plate 2. Further, this arrangement allows bubbles produced around cells 20 to be removed easily, accordingly enabling the pharmaceutical to be applied to cells 20 without fail.

Figure 14:
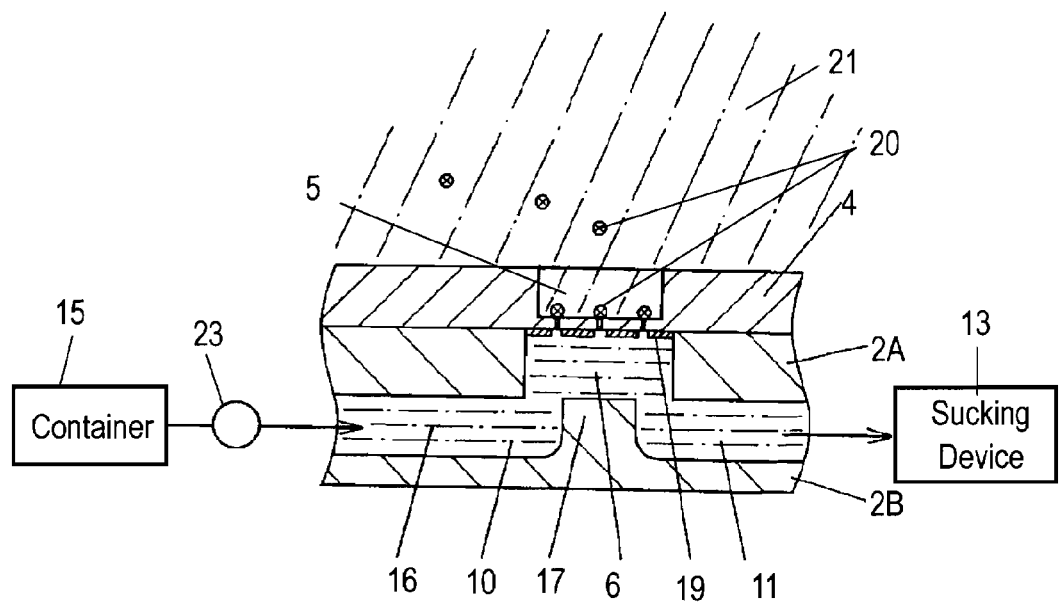
FIG. 14 is a sectional view of the probe in accordance with Embodiment 1.

When valve 23 is opened in the Giga-Seal shown in FIG. 12, measurement solution 16 in container 15 is sucked into flow passage 10 and cavity 6, as shown in FIG. 14. Thus, container 15 functions as a pouring device for introducing measurement solution 16 into flow passage 10. Flow passage 11 is decompressed by sucking device 13, and accordingly, portion 21B of solution 21 in cavity 6 is replaced by measurement solution 16. Measurement solution 16, including a large concentration of $K^+$, allows the change in the electrical potential of cells 20 to be measured more accurately.

Reference electrode 18 and measuring electrode 19 may be formed near openings 9A and 9B of through-holes 9 by a thin-film technique to detect the change in the electric potential of target cell 20.

Figure 15:
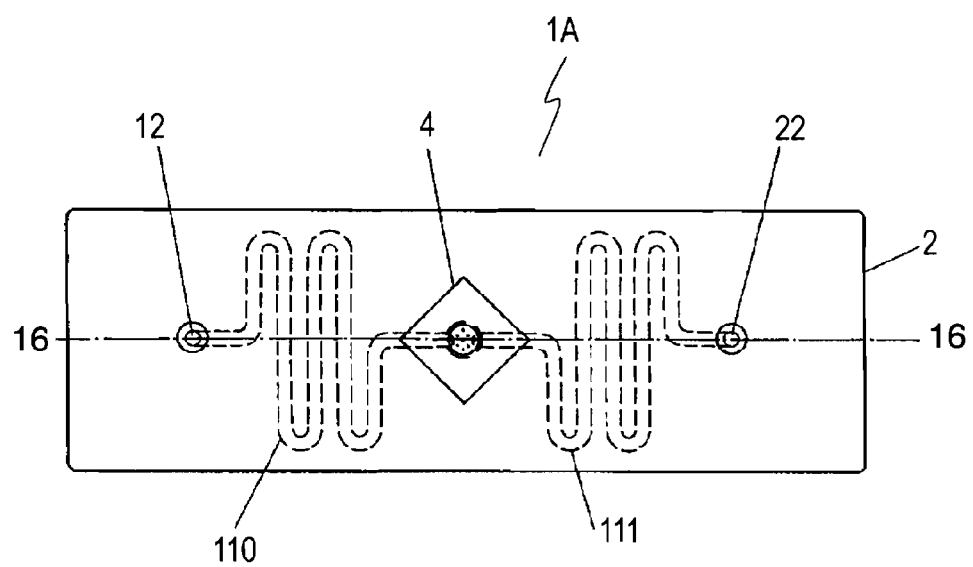
FIG. 15 is a plan view of another probe for measuring an electric potential of a cell in accordance with Embodiment 1.

FIG. 15 is a plan view of another probe 1A for measuring an electric potential of a cell in accordance with Embodiment 1. Each of flow passages 110 and 111 has a curved portion. This structure provides a large resistance to the flow of the fluid passing through passages 110 and 111, accordingly preventing culture solution 21 and measurement solution 16 flowing into cavity 6 from leaking to outside, and from having bubbles in the solutions from outside.

Figure 16A:
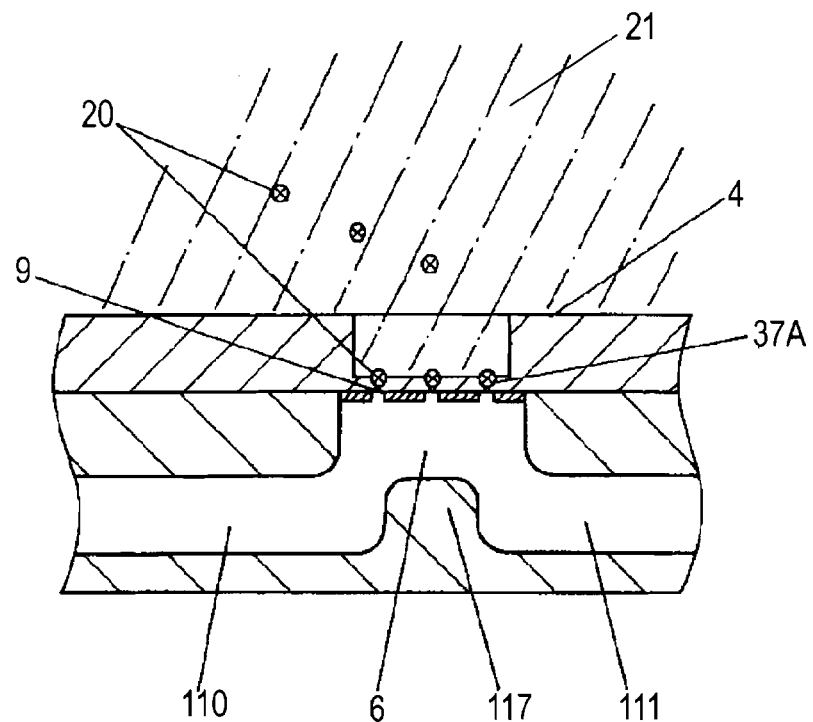
FIG. 16A is an enlarged sectional view of the probe shown in FIG. 15.

FIG. 16A is an enlarged sectional view of probe 1A at line 16-16 shown in FIG. 15. Pocket 37A having a diameter larger than that of through-hole 9 is provided at opening 9A of through-hole 9 facing cavity 5 as to catch the target cell more securely.

Figure 16B:
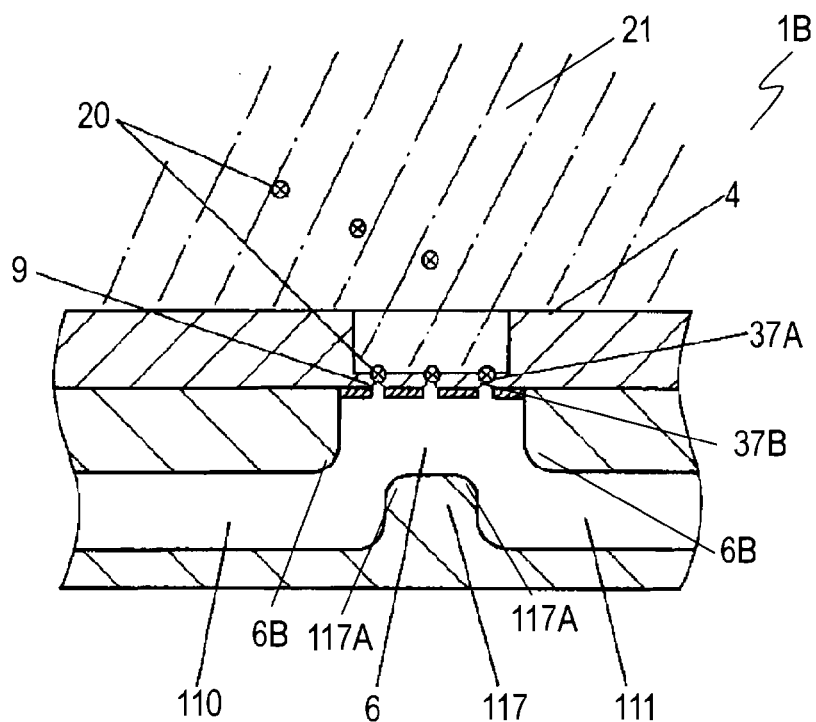
FIG. 16B is an enlarged sectional view of still another probe for measuring an electric potential of a cell in accordance with Embodiment 1.

FIG. 16B is an enlarged sectional view of still another probe 1B in accordance with Embodiment 1. In probe 1B, pocket 37B having a diameter larger than that of through-hole 9 is provided at openings 9B of through-holes 9 facing cavity 6. This structure stabilizes the fluidity of culture solution 21 in cavity 6 and the fluidity of measurement solution 16 near openings 9B of through-holes 9.

As shown in FIGS. 16A and 16B, edge 117A of bump 117 and edge 6B of cavity 6 are chamfered to have rounded shapes, thereby allowing measurement solution 16 to flow smoothly.

The insulating material, resin or glass, of plate 2 may be transparent to transmit visible light through the material. This structure allows the user to observe openings 9A of through-holes 9 easily from cavity 6 with a microscope. Hence, monitoring culture solution 21 and measurement solution 16 flowing into cavity 6 as well as presence of bubbles, a user can measure the electric potential of target cell 20.

Thin plate 8 of sensor element 4 may be made of transparent material, such as resin or glass, transmitting visible light therein. This structure allows a user to observe target cell 20 from below the lower surface of plate 2 with a microscope.

Exemplary Embodiment 2

Figure 17:
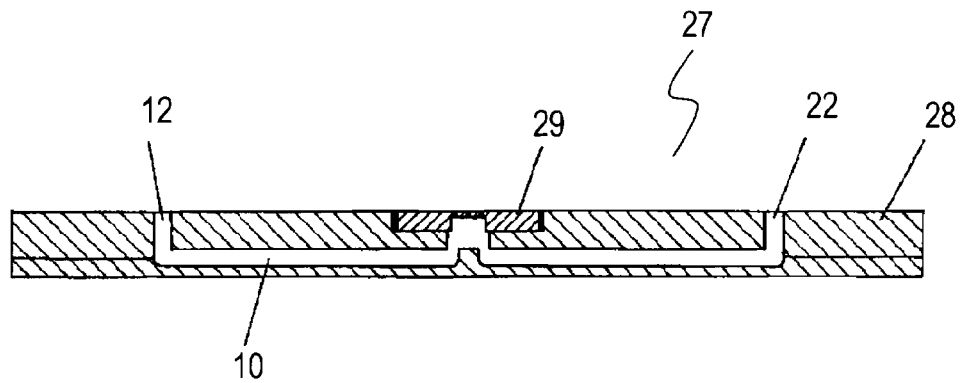
FIG. 17 is a sectional view of a probe for measuring an electric potential of a cell in accordance with Exemplary Embodiment 2 of the invention.
Figure 18:
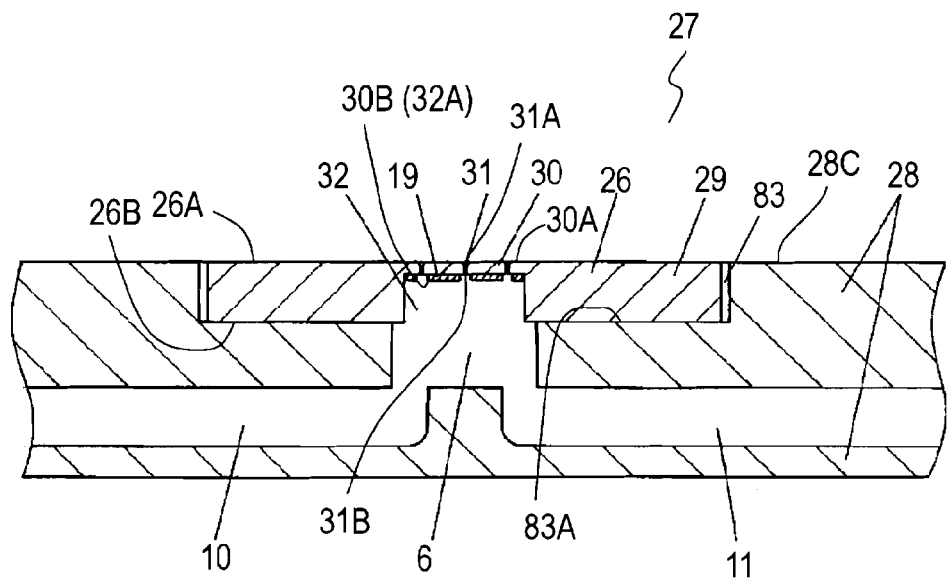
FIG. 18 is an enlarged sectional view of the probe in accordance with Embodiment 2.

FIG. 17 is a sectional view of probe 27 for measuring an electric potential of a cell in accordance with Exemplary Embodiment 2 of the present invention. FIG. 18 is an enlarged sectional view of sensor element 29 of probe 27. Components identical to those of Embodiment 1 are denoted by the same reference numerals, and their descriptions will be omitted.

Probe 27 includes plate 28 and sensor element 29. Upper surface 28C of plate 28 has cavity 83 provided therein. Cavity 6 is provided in bottom surface 83A of cavity 83. Sensor element 29 is fit into cavity 83. Sensor element 29 includes supporting substrate 26. Supporting substrate 26 has lower surface 26B having cavity 32 provided therein. Thin plate 30 is provided at bottom surface 32A of cavity 32. Thin plate 30 has through-holes 31 allowing upper surface 30A of plate 30 to communicate with lower surface 30B (bottom surface 32A of cavity 32) of plate 30. Opening 31A of each of through-holes 31 opens at upper surface 30A of thin plate 30 (upper surface 26A of supporting substrate 26) and communicates with the outside. Opening 31B of each of through-holes 31 opens at lower surface 30B of thin plate 30 and communicates with cavity 32 and cavity 6. Thus, through-holes 31 communicate with flow passages 10 and 11 via cavity 6 provided in plate 28. Measuring electrode 19 is provided on lower surface 30B of thin plate 30 upon necessary.

Figure 19A:
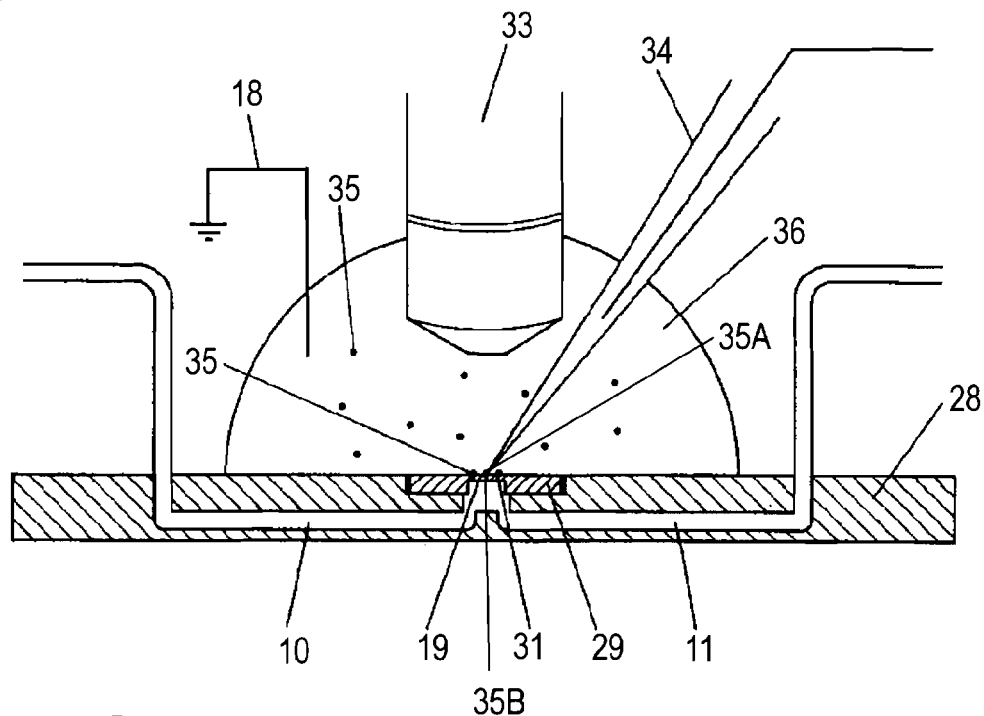
FIG. 19A is a sectional view of the probe for illustrating its usage in accordance with Embodiment 2.
Figure 19B:
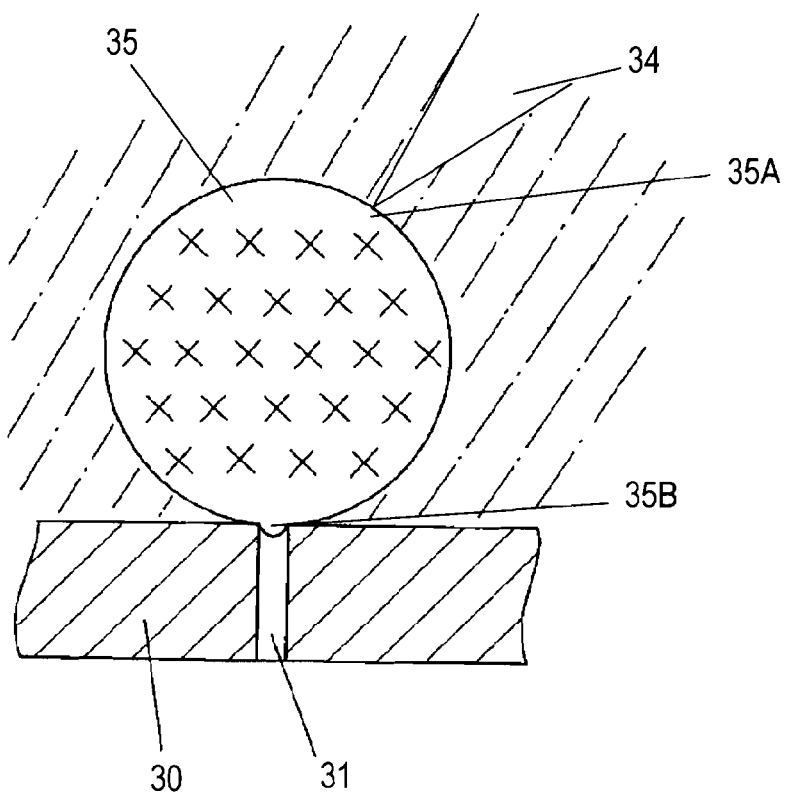
FIG. 19B is an enlarged sectional view of the probe shown in FIG. 19A.

FIG. 19A is a sectional view of probe 27 for illustrating its usage. FIG. 19B is an enlarged sectional view of probe 27 shown in FIG. 19A. Similarly to probe 1 of Embodiment 1, upper surface 26A of supporting substrate 26 of sensor element 29 is flush with upper surface 28C of plate 28, so that no bump or dip is provided thereon. This structure allows target cell 35 to be observed more closely to the cell with microscope 33. Observing cells 35 with microscope 33, a user can attach patch probe 34 to cell 35. This operation allows the user to measure ion-channel activity at plural portions of cell 35. For instance, when pharmaceutical is put into culture solution 36, the probe can detect simultaneously two electric potentials: an electric potential of patch probe 34 attached to portion 35A near an applying position where cell 35 is supplied; and an electric potential of measuring electrode 19 near portion 35B of cell 35 caught at through-holes 31. Portion 35A is farther from the applying position than portion 35A. This simultaneous detection of those two electric potentials allows a transferring state from portion 35A to portion 35B of ion-channel activity in cell 35 to be detected.

As well as probe 1, plate 2, and supporting substrate 7 of Embodiment 1, plate 28 and thin plate 30 of probe 27 may be made of transparent material transmitting visible light therethrough, providing effects similar to those of Embodiment 1.

Exemplary Embodiment 3

Figure 20:
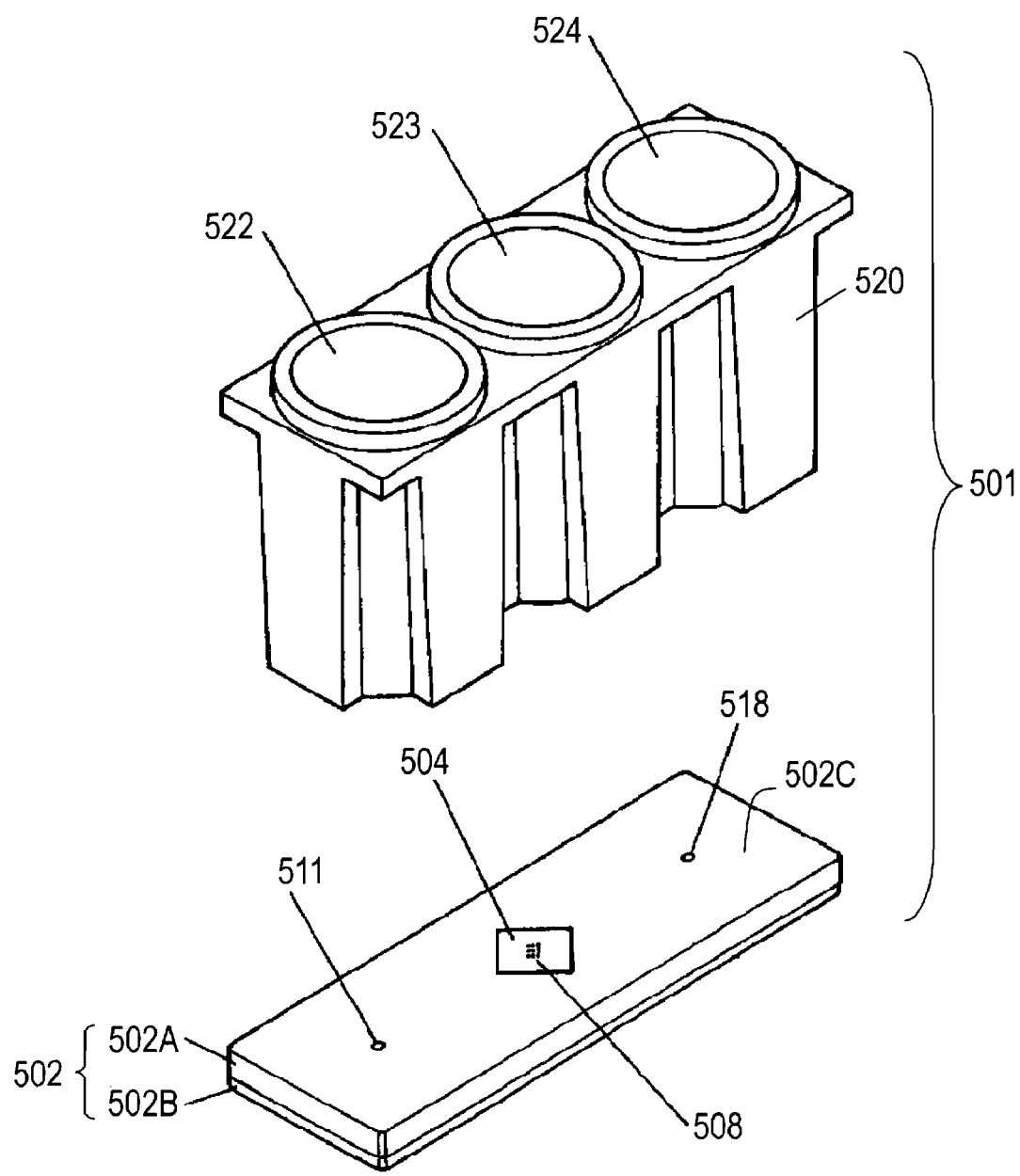
FIG. 20 is an exploded perspective view of a probe for measuring an electric potential of a cell in accordance with Exemplary Embodiment 3 of the invention.
Figure 21:
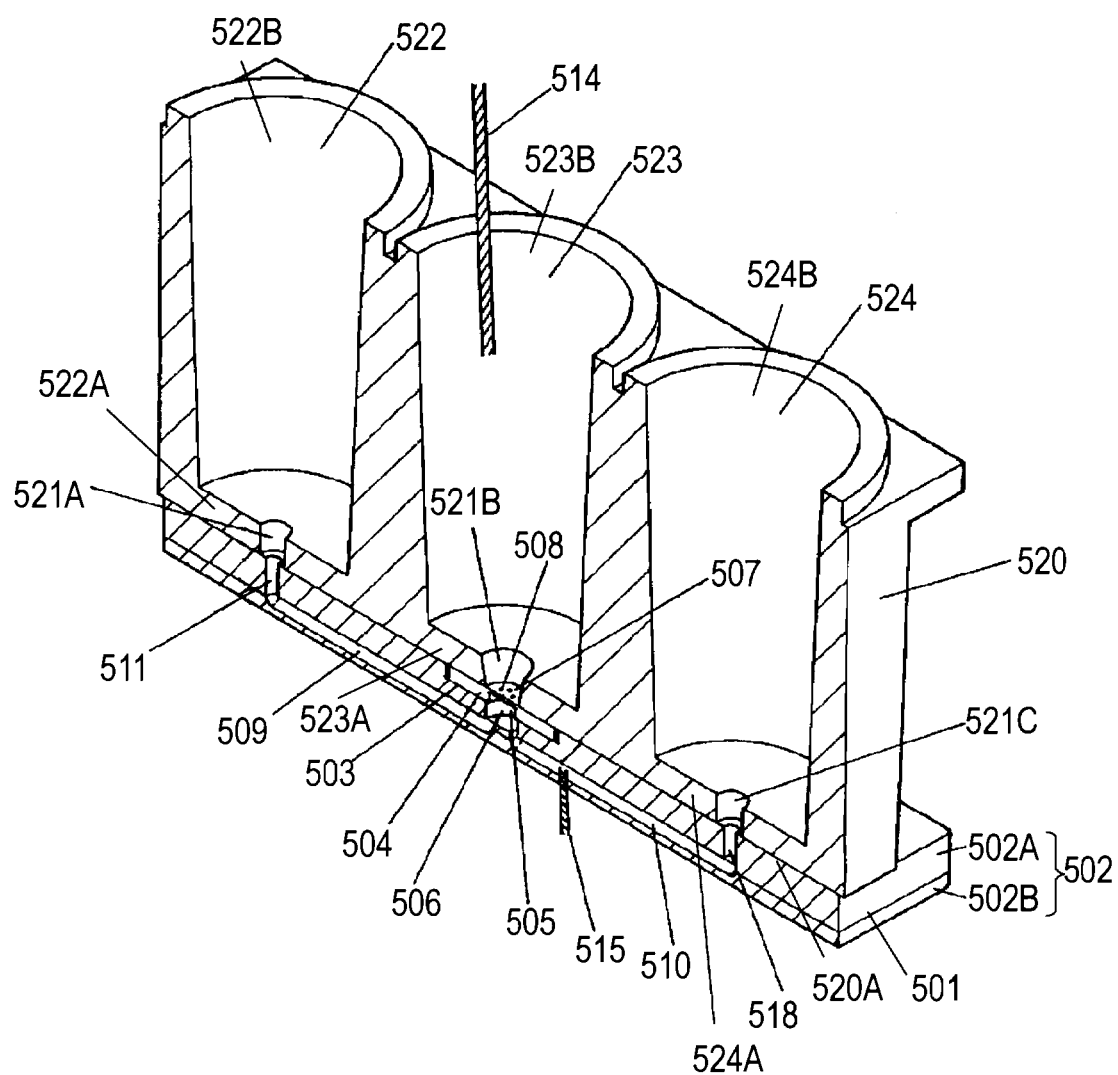
FIG. 21 is a sectional perspective view of the probe in accordance with Embodiment 3.
Figure 22:
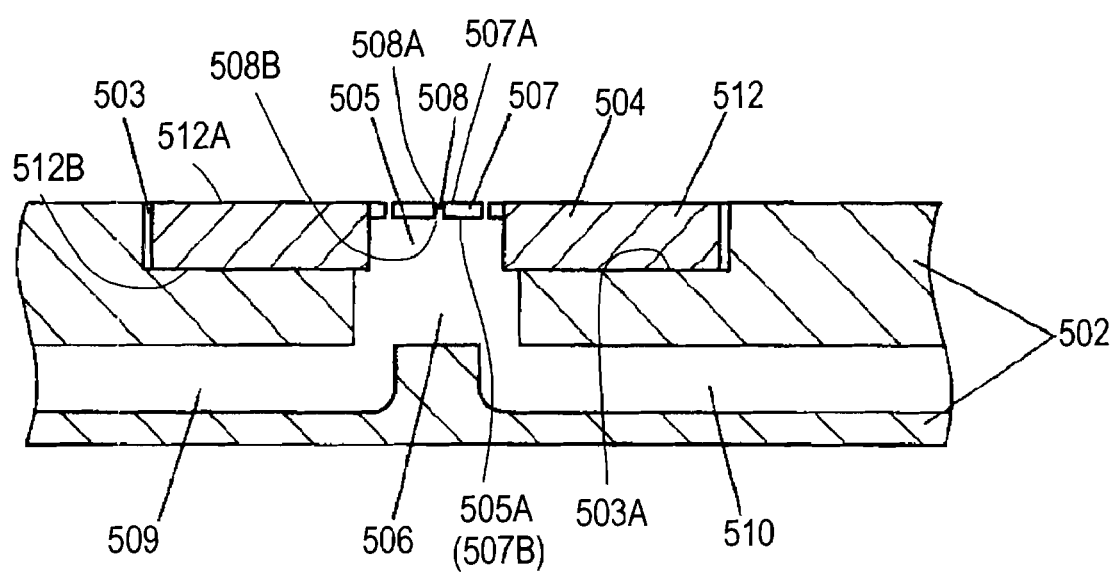
FIG. 22 is an enlarged sectional view of the probe in accordance with Embodiment 3.

FIG. 20 is an exploded perspective view of probe 501 for measuring an electric potential of a cell in accordance with Exemplary Embodiment 3 of the present invention. FIG. 21 is a sectional perspective view of probe 501. FIG. 22 is an enlarged sectional view of an essential part of probe 501. Probe 501 includes plate 502, sensor element 504, and well array 520. Plate 502 is made of insulating material, such as resin or glass. Upper surface 502C of plate 502 has cavity 503 provided therein. Bottom surface 503A of cavity 503 has cavity 506 provided therein. Sensor element 504 is fit into cavity 503. Cavity 506 is positioned below sensor element 504.

Cavity 506 is connected with flow passages 509 and 510 communicating with the outside. Flow passage 509 has opening 511 thereof provided in upper surface 502C of plate 502. Flow passage 510 has opening 518 thereof provided at upper surface 502C. Flow passages 509 and 510 communicate with the outside of plate 502. Molded plate 502A previously molded is stuck on molded plate 502B previously molded, thus providing plate 502. Flow passages 509 and 510 having groove shapes are provided in molded plate 502B. Openings 511 and 518 shaped like through-holes are provided in molded plate 502A. Cavities 503 and 506 provided in molded plate 502A are shaped like a through-hole and communicate with each other.

Sensor element 504 includes supporting substrate 512 and thin plate 507. As shown in FIG. 22, cavity 505 is provided below thin plate 507 (at the side of lower surface 512B of plate 502 opposite to upper surface 502C about plate 502). In other words, thin plate 507 provides bottom surface 505A of cavity 505. Thin plate 507 has small through-holes 508 allowing upper surface 507A (upper surface 512A of supporting substrate 512) to communicate with lower surface 507B. Openings 508A of through-holes 507 provided at upper surface 507A (upper surface 512A of supporting substrate 512) hold target cells, respectively. Through-holes 508 necessarily have diameters smaller than the sizes of the target cells. Similarly to the probe shown in FIG. 16A, a pocket having a diameter larger than that of through-hole 508 may be provided at each of openings 508A to hold the target cell securely and stably. Each of through-hole 508 has opening 508B which opens to cavity 505 at lower surface 507B (lower surface 505A of cavity 505) of thin plate 507. Opening 508A of through-hole 508 communicates with upper surface 512A of substrate 512 of sensor element 504. Opening 508B of through-hole 508 communicates with cavity 506 via cavity 505. This structure allows liquid, such as culture solution and chemicals, to flow in through-holes 508 and cavities 505 and 506.

In sensor element 504, thin pate 507 is placed at the upper part, that is, upper surface 512A of supporting substrate 512 and upper surface 502C of plate 502 are positioned in a single, common plane. However, similarly to the probe shown in FIG. 6 in accordance with Embodiment 1, cavity 505 may be provided in upper surface 512A of supporting substrate 512.

Well array 520 is placed on upper surface 502A of plate 502. Well array 520 has a predetermined capacity for receiving, storing, or circulating liquid, such as culture solution and chemicals, therein. Well array 520 has wells 522, 523, and 524 provided therein. Lower surface 522A of well 522 has through-hole 521A provided therein and communicates with opening 511 of flow passage 509. Lower surface 523A of well 523 has through-hole 521B provided therein and communicates with through-hole 508 provided in thin plate 507 of sensor element 504. Lower surface 524A of well 524 has through-hole 521C provided therein and communicates with opening 518 of flow passage 510. Wells 522, 523, and 524 have openings 522B, 523B, and 524B at their tops, respectively, for receiving culture solution or chemicals. Reference electrode 514 is provided in well 523. Measuring electrode 515 is provided in flow passage 510 and is drawn out to the outside of plate 502.

Culture solution containing the target cells is introduced into well 523 from opening 523B, and is sucked from opening 524B of well 524 with a sucking device, such as a suction pump. The culture solution accordingly flows in through-holes 508 and is sucked into well 524 via cavities 505 and 506, flow passage 510, and opening 518. Alternately, measurement solution or culture solution is introduced into well 522, and is sucked from well 524. Then, the solution sufficiently fills flow passages 509 and 510 and cavities 505 and 506, and is prevented from producing bubbles therein, thereby providing accurate measurement. In this case, the measurement solution may be introduced preferably before the target cells are input in well 523 so as to sufficiently fill flow passages 509 and 510. Then, opening 522 of well 522 is closed, and after that, the cells are input into well 523 while the measurement solution is sucked from well 524.

Since through-holes 508 of sensor element 504 have the diameters small enough to preventing the target cells from passing through the holes, the cells can be held at openings 508A of holes 508, thereby having electric potentials measured while held at through-holes 508. According to Embodiment 3, thin plate 507 has plural through-holes 508 provided therein, thus measuring the electric potentials of the cells at once. After the target cells clogs all of through-holes 508, the other cells remain in well 523. Then, the amount of the culture solution flowing into cavity 505 accordingly decreases, and it is accordingly detected that the cells are held at openings 508A of through-holes 508. This operation can be performed by controlling a suctioning force at well 524 while measuring a flow rate of the culture solution. The suctioning may be performed from well 522, providing the same effects.

Opening 523B of well 523 is closed. Then, chemicals is introduced into well 522 and is sucked from well 524 with the sucking device, accordingly flowing in through-hole 521A, through opening 511, flow passage 509, cavities 506 and 505, flow passage 510, and opening 518, and then being sucked into well 524. At this moment, the chemicals contact, through openings 508B of holes 508, the target cells trapped at openings 508A of through-holes 508, causing the cells to react with the chemicals. The electric potentials of the cells produced due to the reaction can be measured through reference electrode 514 contacting the culture solution in well 523 and through measuring electrode 515 contacting the chemicals in flow passage 510.

Probe 501 allows liquids, such as culture solution and chemicals, different from each other to be introduced into well 523 having the target cells therein and flow passage 510 having measuring electrode 515 therein, respectively. Sucking the solution between well 522 and well 524 allows one solution to be replaced easily by the other solution.

Well array 520 having three wells 522, 523, and 524 and its usage have been described. There is a case that chemicals, instead of the culture solution, are introduced into well 523 to measure just the electric potential of the cells after the target cells are held at small through-holes 508. In this case, the well array may have only two wells (for example, wells 523 and 524) therein as to perform the measurement.

Upper surface 502C of plate 502 is attached securely onto bottom surface 520A of well array 520 to enable well array 520 to seal plate 502 securely, thereby preventing the solution securely from leakage.

Well array 520 may be made of material identical to that of plate 502, hence preventing their deformation due to a difference between respective expansion coefficients of the materials, and thereby sealing plate 502 securely.

Well array 520 and plate 502 may be made of thermoplastic resin, such as polystyrene, cycloolefin polymer, or cycloolefin copolymer, hence providing a secure sealing by ultrasonic fusion or laser welding, and allowing probe 501 to be manufactured at a high productivity.

Well array 520 and plate 502 may be made of glass material or quartz material. These materials can have surfaces directly bonded onto each other without an adhesive if the surfaces are polished to be finished in mirror-like. Each of these materials has a large resistance to heat, thus being bonded to each other with non-organic adhesive, such as glass adhesive or ceramic adhesive. Well array 520 and plate 502 made of these materials have large heat resistance, hence providing probe 501 re-usable by heat-washing.

As shown in FIG. 21, at least through-hole 521B out of through-holes 521A, 521B, and 521C provided in lower surfaces 522A, 523A, and 524A of wells 522, 523, and 524, respectively, may flare toward opening 523B of well 523, that is, may taper towards through-hole 508 of sensor element 504. This structure introduces the culture solution or chemicals which are put into well 523, into through-holes 508 of sensor element 504 quickly.

As shown in FIG. 21, through-hole 521B has a size larger than that of thin plate 507 having through-holes 508 provided therein, allowing the target cells to be introduced efficiently into through-holes 508.

Well array 520 has well 523 having the culture solution containing the target cells input thereinto, well 522 having the chemicals input thereinto, and well 524 coupled with the sucking device. This structure allows upper surface 502C of plate 502 to hold the target cells easily, and allows operations, such as the inputting of the chemicals, to be performed independently from above well array 520, thus allowing probe 501 to be manipulated easily for measuring the electric potential.

Through-hole 521A of well 522 has a size larger that of opening 511 of flow passage 509, and through-hole 521C of well 524 has a size larger than that of opening 518 of flow passage 510. This structure can introduce liquid, such as the chemicals, quickly into the flow passages, allowing probe 501 to measure the electric potential of the cells accurately with little variation.

Reference electrode 514 is provided in well 523 at a predetermined position contacting the culture solution. Measuring electrode 515 is provided in flow passage 510 and contacts the liquid, such as the culture solution or the chemicals, in flow passage 510. This structure can measure an electric potential of the target cell in the culture solution and an electric potential of the cell after the liquid, such as the chemicals is input from well 522 or well 523, thus measuring the change between the above potentials. Measuring electrode 515 may be provided near cavity 505 or cavity 506.

Reference electrode 514 and measuring electrode 515 are made of wires or thin-film electrodes, and are coupled to a measuring instrument outside probe 501 for detecting signals from those electrodes.

A method of measuring an electric potential of the cells with probe 501 will be described below.

First, the culture solution containing the target cells is introduced into well 523, and is sucked with by the sucking device from well 522 or well 524 for holding the cells at through-holes 508 of sensor element 504. An electric resistance between reference electrode 514 which contacts the culture solution and is provided in well 523, and measuring electrode 515 provided in flow passage 510 is measured. A suctioning pressure of the suction device is controlled so that the resistance between electrodes 514 and 515, that is, the resistance between the culture solution stored in well 523 and the culture solution stored in flow passage 510 exceeds 100

MΩ. Reference electrode 514 and measuring electrode 515 are made of conductive material, such as Au, Ag, or AgCl, and contact the culture solution to be connected electrically with the solution. Therefore, the positions of electrodes 514 and 515 are not limited to the positions described in above.

Next, the measurement solution, such as chemicals, are stored in well 522 and is sucked from well 524, thereby causing the culture solution in flow passage 509, cavities 505 and 506, and flow passage 510 to be replaced by the measurement solution. Thus, solutions, such as the culture solution and the measurement solution, different from each other can be introduced easily into well 523 having the cells therein and cavity 506 having measuring electrode 515 therein, respectively. This operation allows the electric potential of the cells to be measured quickly.

Even if respective functions of well 522 and well 524 are replaced by each other, the electric potential of the cells can be measured.

Wells 522, 523, and 524 may have valves or lids, allowing the measurement of the electric potentials with probe 5 to be controlled easily.

Figure 23:
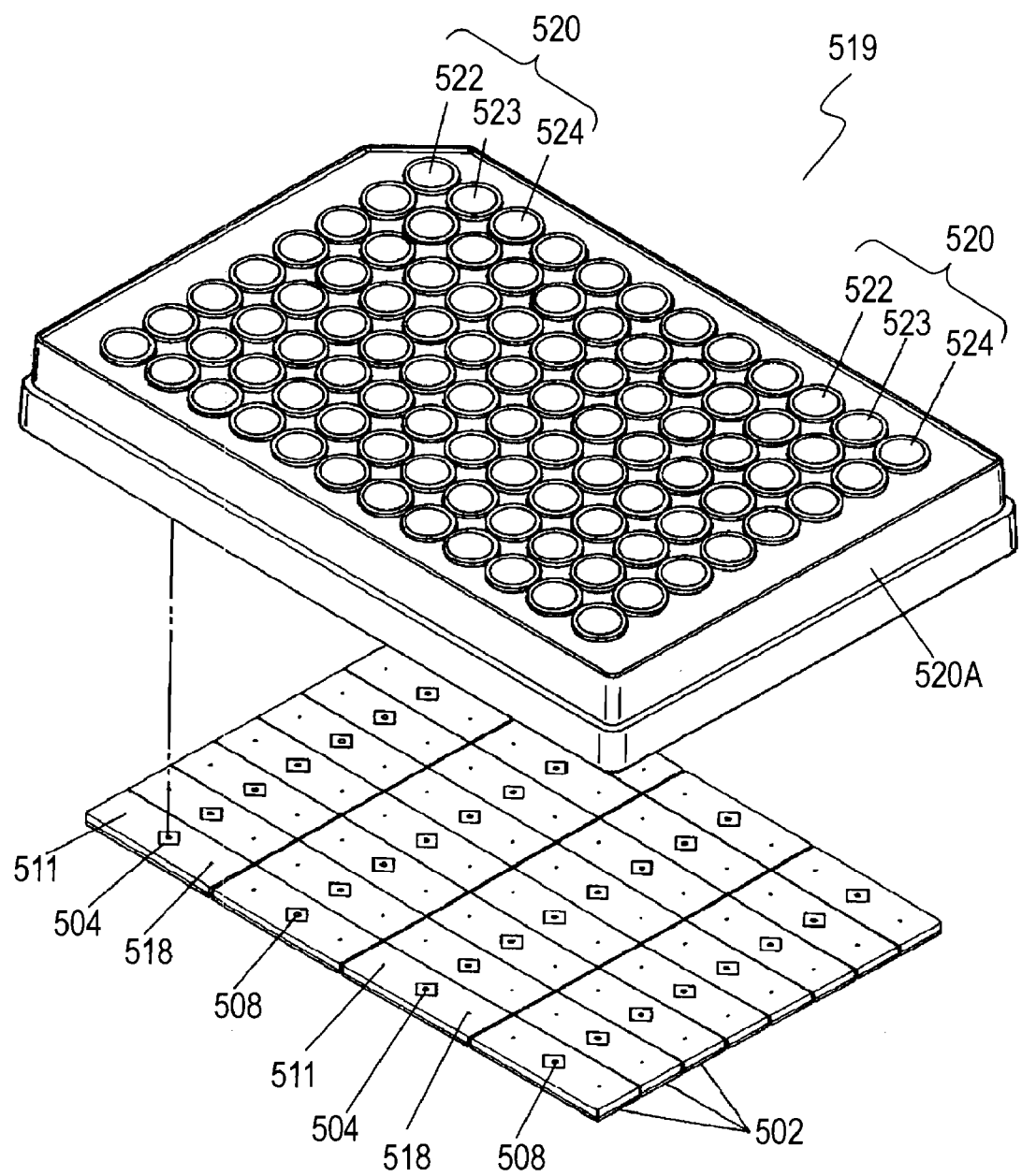
FIG. 23 is a perspective view of a probe array for measuring an electric potential of a cell in accordance with Embodiment 3.
Figure 24:
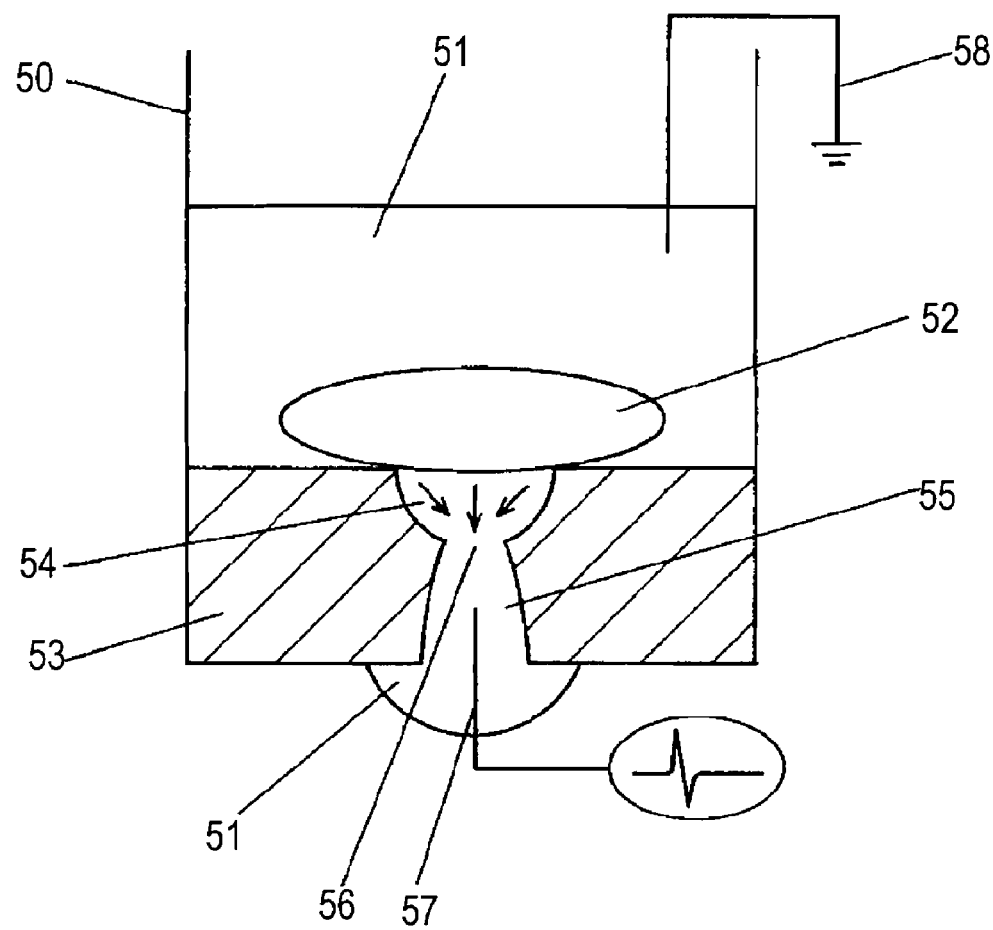
FIG. 24 is a sectional view of a conventional probe for measuring an electric potential of a cell.

Another probe 519, probe array 519, including plural probes 501 in accordance with Embodiment 3 will be described below. FIG. 23 is an exploded perspective view of probe 519 (probe array 519) for measuring an electric potential of a cell. Probes 501 are arranged in a matrix having four rows and eight columns. Plural well arrays 520 each having wells 522, 523, and 524 can be manufactured at once as well array unit 520A.

Probe array 519 including plural probes 501 arranged in a predetermined arrangement allows a robot to pour the chemicals, to input cells, and to suck the cells. Thus, probe 519 can measure respective electric potentials of a lot of cells in a short time for determining pharmacological effect, thus screening candidate pharmaceuticals quickly.

INDUSTRIAL APPLICABILITY

A probe for measuring an electric potential of a cell according to the present invention can measure electric potentials of cells floating in solution as they are in environment, hence being used for determining pharmacological effects to the cells and for screening pharmaceuticals.

The invention claimed is:

1. A probe for measuring an electric potential of a cell, said probe being configured for use with a sucking device, said probe comprising:
    a plate having a surface;
    a first cavity provided in the surface of the plate, the first cavity having a bottom surface;
    a second cavity provided in the bottom surface of the first cavity;
    a first flow passage provided in the plate, the first flow passage having a first opening and a second opening, the first opening of the first flow passage opening to the second cavity, the second opening of the first flow passage opening outside the plate;
    a second flow passage provided in the plate, the second flow passage having a first opening and a second opening, the first opening of the second flow passage opening to the second cavity, the second opening of the second flow passage opening outside the plate;
    a sensor element provided in the first cavity, the sensor element including a thin plate and a supporting substrate, the thin plate having a first surface and a second surface opposite to the first surface;
    a through-hole provided in the thin plate, the through-hole having a first opening which opens to the first surface of the thin plate and a second opening which opens to the second surface of the thin plate and the second cavity of the plate;
    a measuring stick having a first end and a second end, the first end being connected with the plate;
    a first tube having a first end connected to the second opening of the first flow passage and having a second end opposite to the first end of the first tube, the first tube extending along the measuring stick to the second end of the measuring stick; and
    a second tube having a first end connected to the second opening of the second flow passage and having a second end opposite to the first end of the second tube, the second tube extending along the measuring stick to the second end of the measuring stick,
    wherein the supporting substrate of the sensor element is provided in the first cavity of the plate,
    wherein the first flow passage is configured to allow fluid to flow from the first tube into the plate through the second opening of the first flow passage, and
    wherein the sucking device is operable to suck the fluid flowing in the first flow passage through the second end of the second flow passage and through the second tube so as to hold the cell on the first opening of the through-hole of the thin plate.

2. The probe of claim 1, wherein the bottom surface of the first cavity and the second surface of the thin plate of the sensor element are flush with each other.

3. The probe of claim 2, wherein
    the supporting substrate of the sensor element has a first surface and a second surface, the first surface of the supporting substrate facing in a direction identical to a direction which the surface of the plate faces, the second surface of the supporting substrate being provided on the bottom surface of the first cavity of the plate, and
    a third cavity is provided on the first surface of the thin plate.

4. The probe of claim 1, wherein the supporting substrate of the sensor element is bonded to the plate.

5. The probe of claim 1, further comprising a valve,
    wherein the second opening of the second flow passage is configured to be coupled to a pouring device, and the valve is configured to be connected between the pouring device and the second flow passage.

6. The probe of claim 1, wherein the second flow passage has a sectional area not smaller than 0.01 mm$^2$.

7. The probe of claim 1, wherein the second flow passage has a curved portion.

8. The probe of claim 1, wherein the plate includes a bump which is provided between the first flow passage and the second flow passage, the bump projecting toward the second cavity.

9. The probe of claim 1, wherein the first flow passage has a sectional area not smaller than 0.01 mm$^2$.

10. The probe of claim 1, wherein the first flow passage has a curved portion.

11. The probe of claim 1, further comprising electrodes provided on the sensor element around the first opening of the through-hole and the second opening of the through-hole, respectively.

12. The probe of claim 1, further comprising
    at least one pocket, each pocket of the at least one pocket being provided on at least one of the first opening of the through-hole and the second opening of the through-hole of the thin plate, each pocket of the at least one pocket having a diameter larger than a diameter of the through-hole of the thin plate.

13. The probe of claim 1, wherein the plate comprises a material which transmits light.

14. The probe of claim 13, wherein the material of the plate transmits light such that the second cavity can be monitored from below the surface of the plate.

15. The probe of claim 1, wherein the thin plate of the sensor element comprises a material which transmits light.

16. The probe of claim 15, wherein the material of the thin plate transmits light such that the second cavity can be monitored from above the surface of the plate.

17. The probe of claim 1, wherein the plate includes a bump projecting toward the second cavity.

18. The probe of claim 1, wherein the surface of the plate and the first surface of the thin-plate of the sensor element are flush with each other.

19. The probe of claim 18, wherein
the supporting substrate of the sensor element has a first surface and a second surface, the first surface of the supporting substrate facing in a direction identical to a direction which the surface of the plate faces, the second surface of the supporting substrate is provided on the bottom surface of the first cavity of the plate, and
a third cavity is provided on the first surface of the thin plate.

20. The probe of claim 1, wherein the second opening of the second flow passage is configured to be coupled to a pouring device for supplying fluid into the second opening of the second flow passage.

21. The probe of claim 1, wherein the measuring stick extends away from the plate such that the probe can be submerged in a culture solution with the measuring stick extending through the surface of the culture solution.

22. The probe of claim 1, wherein the tube extends from the first end of the measuring stick to the second end of the measuring stick.

23. The probe of claim 1, wherein the second opening of the first flow passage is configured to be coupled to the sucking device so as to suck the fluid in the first flow passage.

24. The probe of claim 1, wherein the plate is operatively attached to the measuring stick, the first tube, and the second tube such that said probe can be dipped into culture solution having the cell floating therein.

25. The probe of claim 1, wherein the first cavity allows the culture solution to enter in the first cavity, and
wherein the plate is arranged on the measuring stick such that the plate can be dipped in the culture solution while maintaining the second end of the measuring stick, the second end of the first tube, and the second end of the second tube outside of the culture solution.

26. The probe of claim 1, wherein said probe is operable to measure the electric potential of the cell by being dipped into culture solution having the cell floating therein.

27. The probe of claim 1, wherein the first tube is in fluid communication with a container, the container holding the fluid which is sucked by the sucking device.

28. The probe of claim 27, further comprising a valve disposed between the container and the first tube.

29. A probe for measuring an electric potential of a cell, said probe being configured for use with a sucking device, said probe comprising:
a plate having an upper surface;
a first cavity provided in the upper surface of the plate, the first cavity having a bottom surface;
a second cavity provided in the bottom surface of the cavity;
a first flow passage provided in the plate, the first flow passage having a first opening and a second opening, the first opening of the first flow passage opening to the second cavity, the second opening of the first flow passage opening outside the plate;
a sensor element provided in the first cavity, the sensor element having a thickness substantially equal to a depth of the first cavity such that an upper surface of the sensor element is substantially flush with the upper surface of the plate and a lower surface of the sensor element contacts the bottom surface of the first cavity; and
a through-hole provided in the sensor element such that the second cavity is in fluid communication with an external environment at the upper surface of the plate,
wherein the flow passage is configured to allow fluid to flow in the plate such that the sucking device is operable to suck the fluid flowing in the first flow passage, wherein the first flow passage has a curved path including at least three switchbacks, and
a third cavity provided in the upper surface of the sensor element such that a thin plate is formed at the bottom surface of the sensor element, the through-hole being provided in the thin plate of the sensor element.

30. The probe of claim 29, further comprising an electrode contacting the lower surface of the sensor element and extending into the second cavity.

31. The probe of claim 30, wherein the electrode is disposed at the through-hole of the sensor element.

* * * * *